(12) United States Patent
Inukai et al.

(10) Patent No.: US 7,566,307 B2
(45) Date of Patent: Jul. 28, 2009

(54) BLOOD PRESSURE MONITORING APPARATUS

(75) Inventors: Hidekatsu Inukai, Nagoya (JP); Toru Oka, Ichinomiya (JP)

(73) Assignee: Fukuda Denshi Co., Ltd., Tokyo (JP)

( * ) Notice: Subject to any disclaimer, the term of this patent is extended or adjusted under 35 U.S.C. 154(b) by 357 days.

(21) Appl. No.: 11/523,651

(22) Filed: Sep. 20, 2006

(65) Prior Publication Data
US 2007/0066910 A1  Mar. 22, 2007

(30) Foreign Application Priority Data
Sep. 21, 2005  (JP)  ............... 2005-273877

(51) Int. Cl.
*A61B 5/02* (2006.01)
(52) U.S. Cl. ..................... 600/485; 600/500
(58) Field of Classification Search ............. 600/485, 600/500, 495
See application file for complete search history.

(56) References Cited

U.S. PATENT DOCUMENTS

| | | | | |
|---|---|---|---|---|
| 5,876,348 A * | 3/1999 | Sugo et al. | ............ | 600/490 |
| 6,036,652 A * | 3/2000 | Inukai et al. | ............ | 600/493 |
| 6,228,033 B1 * | 5/2001 | Koobi et al. | ............ | 600/483 |
| 6,648,828 B2 * | 11/2003 | Friedman et al. | ............ | 600/506 |
| 7,029,447 B2 * | 4/2006 | Rantala | ............ | 600/485 |
| 7,367,941 B2 * | 5/2008 | Silverman et al. | ............ | 600/300 |
| 2003/0109772 A1 * | 6/2003 | Mills | ............ | 600/310 |

FOREIGN PATENT DOCUMENTS

JP  10-66681  3/1998

* cited by examiner

*Primary Examiner*—Charles A Marmor, II
*Assistant Examiner*—Michael D'Angelo
(74) *Attorney, Agent, or Firm*—Drinker Biddle & Reath LLP (57) ABSTRACT

A blood pressure monitoring apparatus which continuously estimates and monitors the blood pressure by using the pulse wave propagation time can accurately estimate the blood pressure. While an estimated blood pressure is continuously calculated by using the pulse wave propagation time, the correlation between the pulse wave propagation time and the interval between feature points contained in two consecutive heart beat waveforms of an electrocardiogram is monitored. If the correlation is reversed, the blood pressure is actually measured, and the estimated blood pressure is corrected on the basis of the difference between the estimated blood pressure and actually measured blood pressure.

9 Claims, 5 Drawing Sheets

BLOOD PRESSURE MONITORING APPARATUS

CLAIM OF PRIORITY

This application claims priority from Japanese Patent Application No. 2005-273877, filed on Sep. 21, 2005, which is hereby incorporated by reference herein.

BACKGROUND OF THE INVENTION

1. Field of the Invention

The present invention relates to a blood pressure monitoring apparatus for noninvasively and continuously monitoring blood pressure.

2. Description of the Related Art

There are many opportunities for measuring blood pressure for purposes such as a medical examination, a diagnosis of a disease, and daily physical condition check-up. However, but these measurements are generally not continuous measurements. On the other hand, in places such as an operating room and ICU for treating serious patients, continuous blood pressure monitoring is sometimes necessary. An apparatus using blood pressure estimation based on the pulse wave propagation time is conventionally known as a blood pressure monitoring apparatus for noninvasively and continuously monitoring the blood pressure.

The time (pulse wave propagation time) required for a pulse wave to propagate between two points in a living body, or the pulse wave propagation velocity obtained by dividing the blood vessel length between the two points by the pulse wave propagation time has a correlation with the blood pressure. Therefore, the blood pressure can be continuously acquired and monitored by, e.g., continuously measuring the pulse wave propagation time and applying it to an equation having a calibrated coefficient, thereby continuously calculating estimated blood pressures (e.g., Japanese Patent Application Laid-Open No. 10-66681).

To measure the pulse wave propagation time, however, pulse waves must be measured in two different locations of the body, so the measurement is complicated. Also, injuries of the patient or interferences with another medical tool sometimes make it difficult to attach sensors or cuffs for measuring pulse waves to the measurement locations. As described in Japanese Patent Application Laid-Open No. 10-66681, therefore, a general approach is to calculate the pulse wave propagation time by using an electrocardiogram (ECG) which is normally continuously measured by a biological information monitoring apparatus, and a pulse wave measured in one predetermined portion (e.g., a fingertip) of the patient.

This method has a merit in that it is unnecessary to add any dedicated sensor for measuring the pulse wave propagation time. Unfortunately, the use of an ECG in the calculation of the pulse wave propagation time has a demerit that the measurement accuracy of the pulse wave propagation time decreases. That is, an ECG is a signal which represents not a pulse wave but the electrical state change of the heart, so there is a time difference (preejection period) between the timing at which the electrical state change occurs and the timing at which the heart actually contracts to generate a pulse wave. Accordingly, the pulse wave propagation time, calculated by using the observation timing of a feature point of an ECG as a starting point, contains an error caused by the preejection period.

If the preejection period is constant, this error is easy to correct. However, the preejection period changes from one person to another, and can change occasionally even in the same person. Therefore, the accuracy improvement by the correction is limited.

A blood pressure monitoring apparatus normally monitors whether the blood pressure continuously calculated on the basis of the pulse wave propagation time falls within a normal range or not. If the blood pressure is abnormal, a more accurate blood pressure measurement is performed by using a cuff or the like, and an alarm is output if the measurement result is also abnormal.

Blood pressure measurement using a cuff is well-established as a noninvasive blood pressure measuring method, and is effective to automatically obtain a reliable blood pressure. However, this method requires avascularization, so the frequent use of the method is undesirable because the burden on a patient increases. Therefore, to determine the necessity of cuff blood pressure measurement on the basis of an estimated blood pressure, which is calculated by using the pulse wave propagation time calculated from an ECG and a pulse wave observed in one portion of the body, moderate threshold values are set to detect an abnormal blood pressure so that cuff blood pressure measurement is not performed more than necessary due to an error of the estimated blood pressure. If the threshold values are too moderate, however, an abnormality of the true blood pressure also becomes difficult to detect, and this makes appropriate threshold values very difficult to set.

To fundamentally solve this problem, the accuracy of the estimated blood pressure must be increased.

SUMMARY OF THE INVENTION

The present invention has been made in consideration of the problems of the prior art as described above, and has as its object to make it possible to accurately measure the blood pressure in a blood pressure monitoring apparatus which continuously estimates the blood pressure on the basis of the pulse wave propagation time.

According to one aspect of the present invention there is provided a blood pressure monitoring apparatus comprising: blood pressure measuring unit adapted to measure a blood pressure by a predetermined method; electrocardiogram measuring unit adapted to measure an electrocardiogram; pulse wave acquiring unit adapted to acquire a pulse wave in a predetermined location of a living body; pulse wave propagation time calculating unit adapted to calculate a pulse wave propagation time from the pulse wave and, one of the electrocardiogram and a pulse wave acquired from a location different from the predetermined location; estimated blood pressure calculating unit adapted to calculate an estimated blood pressure by using the pulse wave propagation time; interval calculating unit adapted to calculate an interval between feature points contained in two consecutive heart beat waveforms of the electrocardiogram; monitoring unit adapted to monitor one of a first correlation which is a correlation between the pulse wave propagation time and the interval between the feature points, and a second correlation which is a correlation between the estimated blood pressure and the interval between the feature points; and control unit adapted to perform the measurement by the blood pressure measuring unit if the monitoring unit detects that the first correlation has become a negative correlation or the second correlation has become a positive correlation, and controlling the estimated blood pressure calculating unit to correct the estimated blood pressure on the basis of a difference between the measurement result and the estimated blood pressure.

According to this arrangement, in the present invention, the equation for calculating the estimated blood pressure is calibrated by taking account of the fluctuation amount of a waveform parameter which is obtained from an accelerated pulse wave and reflects the functional state of the blood vessel. This makes it possible to increase the calibration accuracy of the equation, thereby increasing the accuracy of the estimated blood pressure.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the present invention will now be described in detail in accordance with the accompanying drawings.

Figure 1:
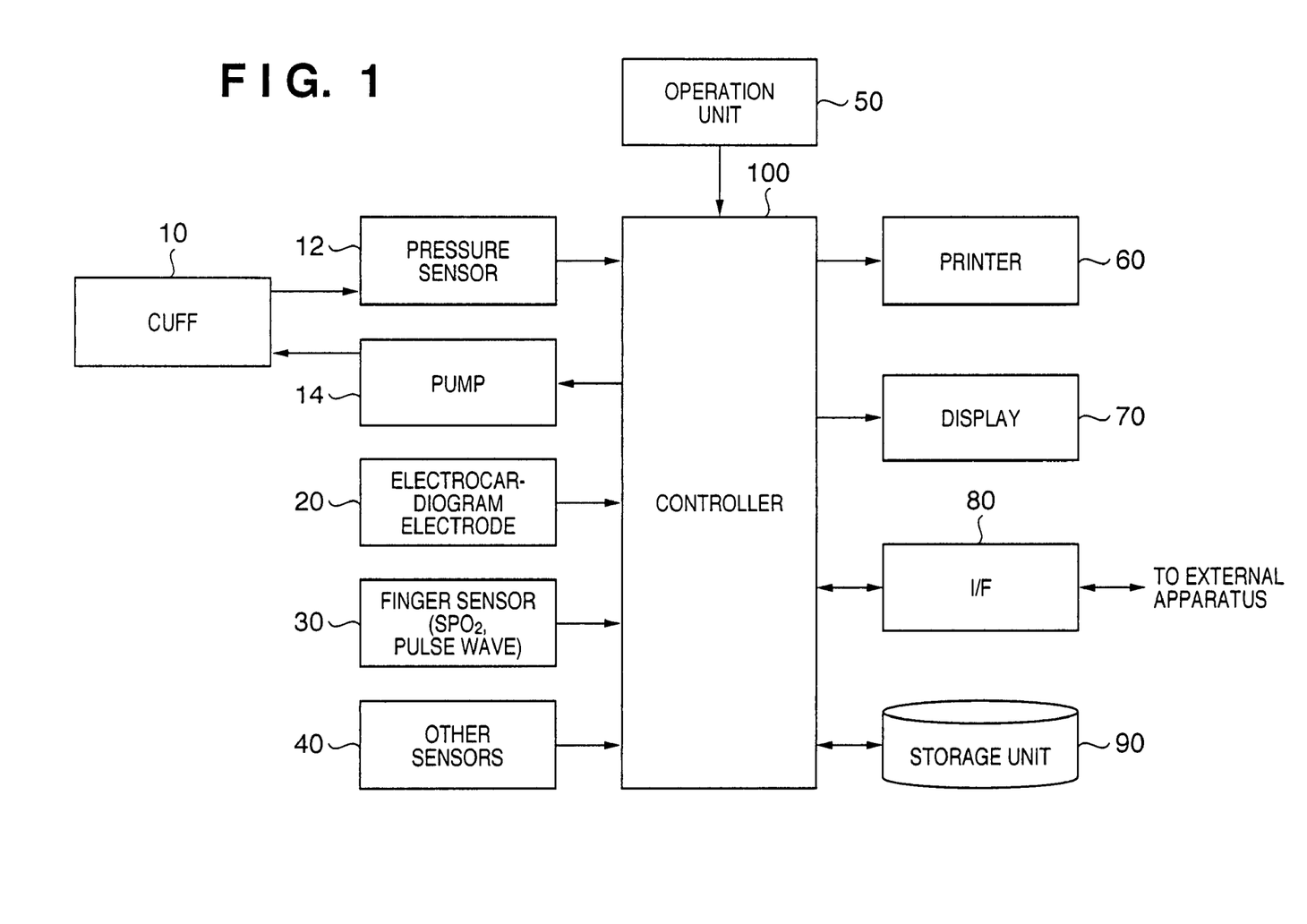
FIG. 1 is a block diagram showing an example of the configuration of a biological information monitoring apparatus as a blood pressure monitoring apparatus according to an embodiment of the present invention.

FIG. 1 is a block diagram showing an example of the functional configuration of a biological information monitoring apparatus as a blood pressure monitoring apparatus according to an embodiment of the present invention.

Referring to FIG. 1, a cuff 10 has a band-like shape, and incorporates a rubber bladder which inflates and deflates by charging and evacuating of a gas by a pump 14. The cuff 10 is normally attached to one of the limbs, typically the upper arm of a patient. A pressure sensor 12 senses a change in pressure applied to the gas filled in the internal rubber bladder of the cuff 10, converts the pressure signal into an electrical signal, and outputs the electrical signal to a controller 100.

An electrocardiogram electrode 20 comprising a plurality of electrodes is attached to a predetermined position of the chest of a patient, and outputs an induced waveform as an electrocardiogram (ECG) signal to the controller 100. A finger sensor 30 is a so-called pulse oximeter which optically senses and outputs an oxygen saturation degree ($SPO_2$) and plethysmograph to the controller 100. The absorbance of light by hemoglobin changes in accordance with whether hemoglobin combines with oxygen as well as in accordance with the wavelength of light. Therefore, the finger sensor 30 generally measures the oxygen saturation degree by using lights with two wavelengths, i.e., by using red light and infrared light. Also, since the AC component of transmitted light or reflected light changes in accordance with the blood flow volume, this AC component is detected as a photoplethysmograph (PTG).

Other sensors 40 sense other biological information such as the respiration and body temperature of a patient, and one or more sensors are connected to the controller 100 as needed. The other sensors 40 are not directly relevant to the blood pressure monitoring operation of this embodiment, so no further explanation thereof will be made.

An operation unit 50 is a man-machine interface by which the user (operator) inputs various settings and information concerning a patient to the biological information monitoring apparatus and gives instructions to it. The operation unit 50 is generally constructed by appropriately combining a keyboard, a mouse, buttons, switches, dials, a touch panel, and the like.

A printer 60 and display 70 are representative output devices, and visually output the state of the apparatus, measurement results, and the like. An external interface (I/F) 80 is typically a network interface, serial interface (e.g., a USB or IEEE1394), modem, or the like, and communicates with an external apparatus which is connected directly or across a network.

A storage unit 90 is representatively a hard disk drive, and records programs for controlling the operation of the biological information monitoring apparatus, various data, measurement results, personal information of patients, and the like. The storage unit 90 may also include at least one type of another storage device, e.g., a device which reads and writes a writable removable medium such as a memory card or optical disk.

The controller 100 controls the operation of the whole biological information monitoring apparatus. The controller 100 has, e.g., a CPU and RAM, and controls the individual units by loading the control programs stored in the storage unit 90 into the RAM and executing the loaded programs by the CPU, thereby implementing processes including the blood pressure monitoring operation (to be described later) of the biological information monitoring apparatus. Note that not all the processes need be executed by software by the CPU. For example, signal processing such as A/D conversion and filtering of signals input from the various sensors may also be assigned to a DSP or dedicated hardware, thereby appropriately using another configuration.

The blood pressure monitoring operation in the biological information monitoring apparatus of this embodiment will be explained below.

The biological information monitoring apparatus of this embodiment is similar to the prior art in that the pulse wave propagation time is continuously calculated by using an ECG and plethysmograph, and the estimated blood pressure is continuously calculated by using an equation having a calibrated coefficient, and that the necessity of blood pressure measurement using a cuff is determined by using the estimated blood pressure.

In this embodiment, however, if the RR interval of the ECG and the change in pulse wave propagation time satisfy specific conditions, in addition to the estimated blood pressure, it is determined that the accuracy of blood pressure estimation based on the pulse wave propagation time has decreased, and that blood pressure measurement using a cuff is necessary. The estimated blood pressure is corrected by detecting the difference between the estimated blood pressure and the result of measurement using a cuff. Also, the equation for calculating the estimated blood pressure is calibrated if necessary. Consequently, it is possible to increase the accuracy of the estimated blood pressure, and accurately determine the necessary of measurement using a cuff.

In an ECG, the time interval between R waves contained in two consecutive heart beats is called an RR interval. The RR interval and the time difference (pulse wave propagation time) between the ECG and plethysmograph normally have a positive correlation with respect to the increase/decrease. That is, when one of the RR interval and pulse wave propagation time increases, the other also increases; when one decreases, the other also decreases. Blood pressure estimation based on the pulse wave propagation time also uses this correlation.

The correlation between the estimated blood pressure and RR interval may also be used as an analogous index. The estimated blood pressure and RR interval normally have a negative correlation in regard to the increase/decrease. That is, when one of the estimated blood pressure and RR interval increases, the other decreases; when one decreases, the other increases.

Accordingly, when the correlation between the RR interval and pulse wave propagation time has changed, especially when this correlation has changed to a negative correlation in which one increases but the other decreases, or when the correlation between the RR interval and estimated blood pressure has changed to a positive correlation in which one increases and the other also increases, the blood pressure value cannot be accurately estimated any longer, and the accuracy of the estimated blood pressure value decreases. In this embodiment, therefore, the correlation between the RR interval and pulse wave propagation time or between the RR interval and estimated blood pressure value is monitored, and cuff measurement is performed if the correlation becomes opposite to the normal correlation. Correction of the estimated blood pressure value is started by detecting the error between the cuff measurement result and the latest estimated blood pressure.

The correction of the estimated blood pressure may be a method of simply adding or subtracting the error to or from the estimated blood pressure value, and may also be a method which calibrates the equation for calculating the estimated blood pressure in accordance with the error. After that, the correlation between the RR interval and pulse wave propagation time or between the RR interval and estimated blood pressure is kept monitored. If the correlation has returned to the normal correlation, the correction of the estimated blood pressure is stopped. The calibration may also be performed by performing cuff measurement when the normal correlation has returned, detecting the error from the estimated blood pressure again, and correcting a measurement value after that.

Figure 2:
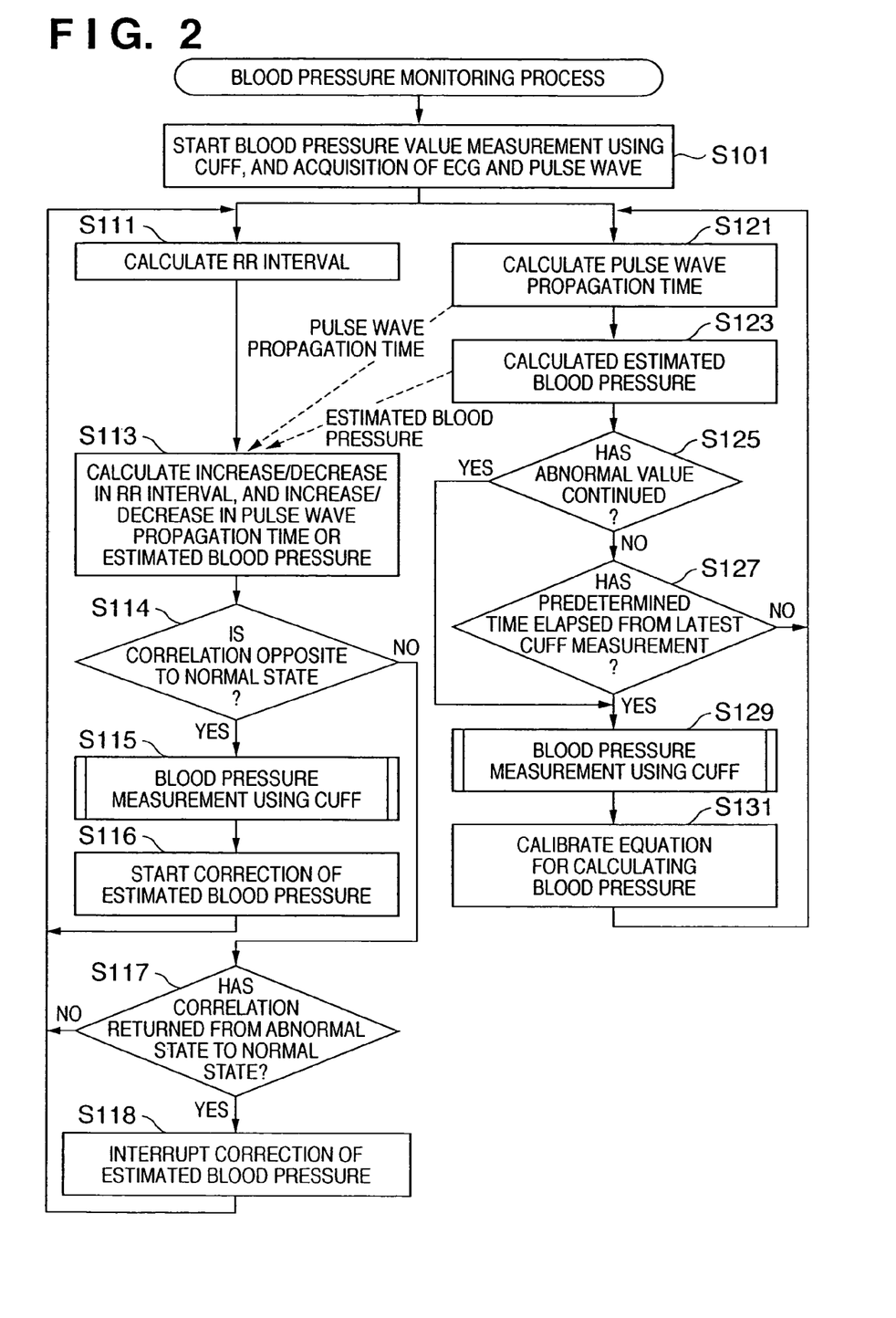
FIG. 2 is a flowchart for explaining the blood pressure monitoring operation of the biological information monitoring apparatus according to the embodiment of the present invention.

On the basis of the above description, the blood pressure monitoring operation of the biological information monitoring apparatus according to this embodiment will be explained with reference to a flowchart shown in FIG. 2.

First, in step S101, the acquisition of an ECG and pulse wave starts. Also, as initialization, initial blood pressure measurement using a cuff is performed, and the initial values of an RR interval, pulse wave propagation time, and estimated blood pressure are calculated by the same methods as explained below, and stored in the storage unit 90. After that, the process (steps S111 to S118) of monitoring the correlation between the RR interval and pulse propagation time or between the RR interval and estimated blood pressure and the process (steps S121 to S131) of estimating the blood pressure on the basis of the pulse wave propagation velocity are performed in parallel.

In step S111, the controller 100 calculates the RR interval of the ECG detected by the electrocardiogram electrode 20. More specifically, the controller 100 detects R waves from the ECG by the well-known method, and calculates the time interval between two adjacent R waves.

In step S113, the controller 100 calculates the increase/decrease (change) in RR interval and the increase/decrease (change) in pulse wave propagation time obtained in step S213 (to be described later), or calculates the increase/decrease (change) in RR interval and the increase/decrease (change) in estimated blood pressure ESYS obtained in step S213 (to be described later).

More specifically, in the former case, the controller 100 obtains the increase/decrease in RR interval from an RR interval RRref measured in the latest blood pressure measurement by using a cuff and an RR interval RRt obtained in step S111. The controller 100 also obtains the increase/decrease in pulse wave propagation time from a pulse wave propagation time DTref measured in the latest blood pressure measurement by using a cuff and a pulse wave propagation time DTt obtained in step S213 (to be described later).

In the latter case, the controller 100 obtains the increase/decrease in RR interval from the RR interval RRref measured in the latest blood pressure measurement by using a cuff and the RR interval RRt obtained in step S111. The controller 100 also obtains the increase/decrease in estimated blood pressure from an estimated blood pressure ESYSref measured in the latest blood pressure measurement by using a cuff and an estimated blood pressure ESYSt obtained in step S213 (to be described later).

For example, the increase/decrease in RR interval is calculated by $DRR=RRref-RRt$ The increase/decrease in pulse wave propagation time is calculated by $DDT=DTref-DTt$ The increase/decrease in estimated blood pressure is calculated by $DESYS=ESYSref-ESYSt$ In step S114, the controller 100 determines whether the correlation between the RR interval and pulse wave propagation time or the correlation between the RR interval and estimated blood pressure is opposite to the normal correlation (whether the former is a negative correlation or the latter is a positive correlation).

Note that in this embodiment, the determination of the correlation in step S114 and in step S117 (to be described later) is done by determining whether a predetermined number of pulses (e.g., 10 pulses) successively have the same correlation, so as not to perform cuff measurement more than necessary. More specifically, the correlation per pulse, obtained from the increase/decrease in pulse wave propagation time and the increase/decrease in estimated blood pressure calculated in step S113, is stored for a predetermined number of pulses measured last, and whether the same correlation continues for a predetermined number of pulses is determined. On the basis of the determination result, the reversal of the correlation (the change from the normal state to the reversed state, or the change from the reversed state to the normal state) is determined.

In the case of the correlation between the RR interval and pulse wave propagation time, if the signs of DRR and DDT are equal, it is determined that the RR interval and pulse wave propagation time have a positive correlation, so the correlation is not reversed.

Note that the difference between RRref and RRt is calculated as the value DRR representing the increase/decrease in this embodiment, but any arbitrary value such as RRref/RRt representing the increase/decrease can be calculated. Note also that any arbitrary value such as DTref/DTt (or ESYSref/ESYSt) representing the increase/decrease can be calculated as the value DDT representing the increase/decrease in pulse wave propagation time (or as the value DSYS representing the increase/decrease in estimated blood pressure value).

To easily recognize the correlation between the RR interval and pulse wave propagation time (or estimated blood pressure value), however, it is preferable to calculate DRR, DDT, and DSYS by the same equations as explained above.

For example, in a case in which DRR=RRref/RRt and DDT=DTref/DTt when the correlation between the RR interval and pulse wave propagation time is to be monitored, if both DRR and DDT are 1 or more or less than 1, it is determined that the correlation is a positive correlation and therefore a normal correlation.

If it is determined in step S114 that the correlation is reversed from the normal correlation (the correlation between the RR interval and pulse wave propagation time has changed to a negative correlation or the correlation between the RR interval and estimated blood pressure has changed to a positive correlation), the storage unit 90 stores a flag, and the flow advances to step S115. If it is determined that the correlation is not reversed but keeps being the normal correlation, the flow advances to step S117.

In step S115, blood pressure measurement using a cuff is performed.

The controller 100 controls the pump 14 to raise the pressure of the cuff 10 to perform avascularization, monitors the input signal from the pressure sensor 12 while gradually exhausting the air after that, and calculates the highest blood pressure value, average blood pressure value, and lowest blood pressure on the basis of the well-known oscillometric method. The controller 100 also stores, in the storage unit 90, the RR interval, pulse wave propagation time, and estimated blood pressure obtained immediately before the blood pressure measurement using the cuff 10, and uses them in the determination of the correlation described above, or in calibration of coefficients a and β contained in the equation for calculating the estimated blood pressure value. Note that during the cuff blood pressure measurement, other processes are interrupted, or the results are ignored.

When the cuff blood pressure measurement is complete, the interrupted processes are resumed, or the ignored processing results are handled as valid. In step S116, the controller 100 calculates the difference (estimated error) between the estimated blood pressure and cuff measurement value stored in the storage unit 90. The controller 100 then starts correcting the estimated blood pressure on the basis of the estimated error, and returns to step S111 to continue processing for the next heart beat. The start of correction of the estimated blood pressure is reflected on processing in step S123 (to be described later).

Various methods can be used to correct the estimated blood pressure value. For example, it is possible to apply one of:

(1) calibrate the equation for calculating the estimated blood pressure value; and (2) correct the estimation result without calibrating the equation for calculating the estimated blood pressure value.

When method (1) which calibrates the equation for calculating the estimated blood pressure is applied, the equation is calibrated in the same manner as in step S131 (to be described later). When method (2) is applied, the estimated error is added to the estimated blood pressure value.

If no reversal of the correlation is found in step S114, the flow advances to step S117, and the controller 100 determines, on the basis of the presence/absence of the flag in the storage unit 90, whether the correlation has returned from the reversed state to the original state (whether the correlation between the RR interval and pulse wave propagation time has returned from a negative correlation to a positive correlation, or the correlation between the RR interval and estimated blood pressure has returned from a positive correlation to a negative correlation). If the correlation has returned to the normal state, the flow advances to step S118, and the controller 100 stops the estimated blood pressure correction which is started when the correlation is reversed to the abnormal state, and deletes the flag in the storage unit 90. After that, the flow returns to step S111.

Note that after step S118, it is also possible to perform cuff blood pressure measurement again, and calibrate the equation for calculating the estimated blood pressure.

If it is determined in step S117 that the normal correlation continues, the flow immediately returns to step S111.

On the other hand, the same blood pressure estimating process as the conventional method is executed in steps S121 to S125.

That is, in step S121, the pulse wave propagation time is calculated on the basis of an ECG detected by the electrocardiogram electrode 20 and a plethysmograph sensed by the finger sensor 30. More specifically, the controller 100 performs signal processing such as noise removal and waveform shaping normally performed on an ECG and plethysmograph, and calculates the time difference between feature points in the individual heart beats of the ECG and plethysmograph as the pulse wave propagation velocity. In this case, the feature point of the ECG can be, e.g., the peak position of an R wave, and the feature point of the plethysmograph can be the leading edge of the waveform. Also, as described earlier, there is a time difference (preejection period) between the appearance of an R wave and the generation of an actual pulse wave. Therefore, correction may also be performed by subtracting a time corresponding to a preejection period statistically calculated beforehand from the time difference between the feature points.

In step S123, an estimated blood pressure is obtained from the calculated pulse wave propagation time.

That is, an estimated blood pressure is calculated by applying the pulse wave propagation time to $$\text{Estimated blood pressure} = a \times (\text{pulse wave propagation time [msec]}) + \beta \quad (2)$$

(a and β are coefficients, a<0, β>0) as disclosed in, e.g., Japanese Patent Laid-Open No. 10-66681.

Note that the coefficients a and β need only be determined in advance. That is, this equation is a linear equation with two unknowns, so the values of the coefficients a and β can be determined by using at least two actually measured blood pressure values and the corresponding pulse wave propagation times.

Note also that each coefficient need not be fixed but may also be updated to an optimum value by using an actually measured blood pressure obtained by another method (cuff measurement or invasive measurement) and the pulse wave propagation time at the corresponding timing.

If correction start is designated in step S116, the corrected estimated blood pressure is obtained in step S123. For example, when correction of adding the estimated error is to be performed, the corrected estimated blood pressure is calculated by Corrected estimated blood pressure=$a$×(pulse wave propagation time [msec])+$\beta$+$d$     (2)'

(a and $\beta$ are coefficients for a<0 and $\beta$>0, and d is the estimated error)

When correction is to be performed by calibrating the equation, coefficients calibrated in the same manner as in step S131 (to be described later) are used as a and $\beta$ in equation (2).

In step S125, the controller 100 determines whether the estimated blood pressure is an abnormal value, and, if the estimated blood pressure is an abnormal value, determines whether the abnormal value has continued for a predetermined time. The abnormal value can be determined by determining whether the estimated blood pressure is larger than the upper limit or smaller than the lower limit of a predetermined normal range, or determining whether the estimated blood pressure fluctuates more than a predetermined amount (which can be either a fluctuation ratio or difference) from the value of the latest cuff blood pressure measurement.

These upper limit, lower limit, or fluctuation amount can be either fixed with-respect to the value of cuff blood pressure measurement, or dynamically changed in accordance with a practical measured blood pressure.

If it is determined in step S125 that the estimated blood pressure has continuously shown an abnormal value for a predetermined time, the flow advances to step S127. If not, the flow returns to step S121 to continue the processing for the next heart beat.

In step S127, whether a predetermined time has elapsed from the latest cuff blood pressure measurement is determined. In the biological information monitoring apparatus of this embodiment as described above, cuff blood pressure measurement is performed whenever a predetermined time has elapsed, even when the state in which the correlation between the RR interval and pulse wave propagation time is not reversed and the estimated blood pressure falls within the normal range continues. If the predetermined time has elapsed since the latest cuff blood pressure measurement, the flow advances to step S129; if not, the flow returns to step S121.

In step S129, cuff blood pressure measurement is performed in the same manner as in step S115. In step S131, the equation for calculating the estimated blood pressure is calibrated on the basis of the measurement result. After that, the flow returns to step S121.

The above processing is repeated until the end of monitoring is designated.

(Equation Calibrating Process)

The process of calibrating the equation for calculating the estimated blood pressure performed in step S131 will be explained in detail below.

As described above, when the result of the cuff blood pressure measurement is obtained at least periodically, the equation for calculating the estimated blood pressure can be calibrated (the coefficients a and $\beta$ can be calibrated) on the basis of the measurement result, thereby increasing the accuracy of the estimated blood pressure during an interval before the next cuff measurement.

In this embodiment, the equation can be calibrated on the basis of the result of the cuff blood pressure measurement, not only when a predetermined time has elapsed from the latest cuff measurement or the estimated blood pressure has continuously shown an abnormal value for a predetermined time, but also when the correlation between the RR interval and pulse wave propagation time (or between the RR interval and estimated blood pressure value) is reversed. As a consequence, the estimation accuracy can increase.

As already described above, the equation for calculating the estimated blood pressure from the pulse wave propagation time can be represented by Estimated blood pressure=$a$×(pulse wave propagation time [msec])+$\beta$     (2)

(a and $\beta$ are coefficients for a<0 and $\beta$>0)

By calibrating these coefficients in accordance with:
- the difference (estimated error) between the blood pressure (actually measured blood pressure) measured by using a cuff and the estimated blood pressure calculated immediately before that; or
- the difference between the latest actually measured blood pressure and the present actually measured blood pressure, it is possible to increase the accuracy of an estimated blood pressure to be calculated after that.

In this embodiment, the coefficient a is corrected as shown in, e.g., Table 1 below.

TABLE 1

| d | Correction Amount of a |
|---|---|
| 30 < d | Recalculate |
| 20 < d ≦ 30 | +10 |
| 10 < d ≦ 20 | +5 |
| −10 ≦ d ≦ 10 | 0 (No correction) |
| −20 ≦ d < −10 | −5 |
| −30 ≦ d < −20 | −10 |
| d < −30 | Recalculate |

Note that d is (estimated blood pressure − actually measured blood pressure) or (actually measured blood pressure (t − 1) − actually measured blood pressure (t)) [mmHg].

If d≧30 or d≦−30, it is determined that simple correction has no effect, so the coefficient is recalculated by using the present actually measured blood pressure and the latest actually measured blood pressure.

The coefficient $\beta$ is also calibrated by using the calibrated coefficient a and the actually measured blood pressure.

Figure 3:
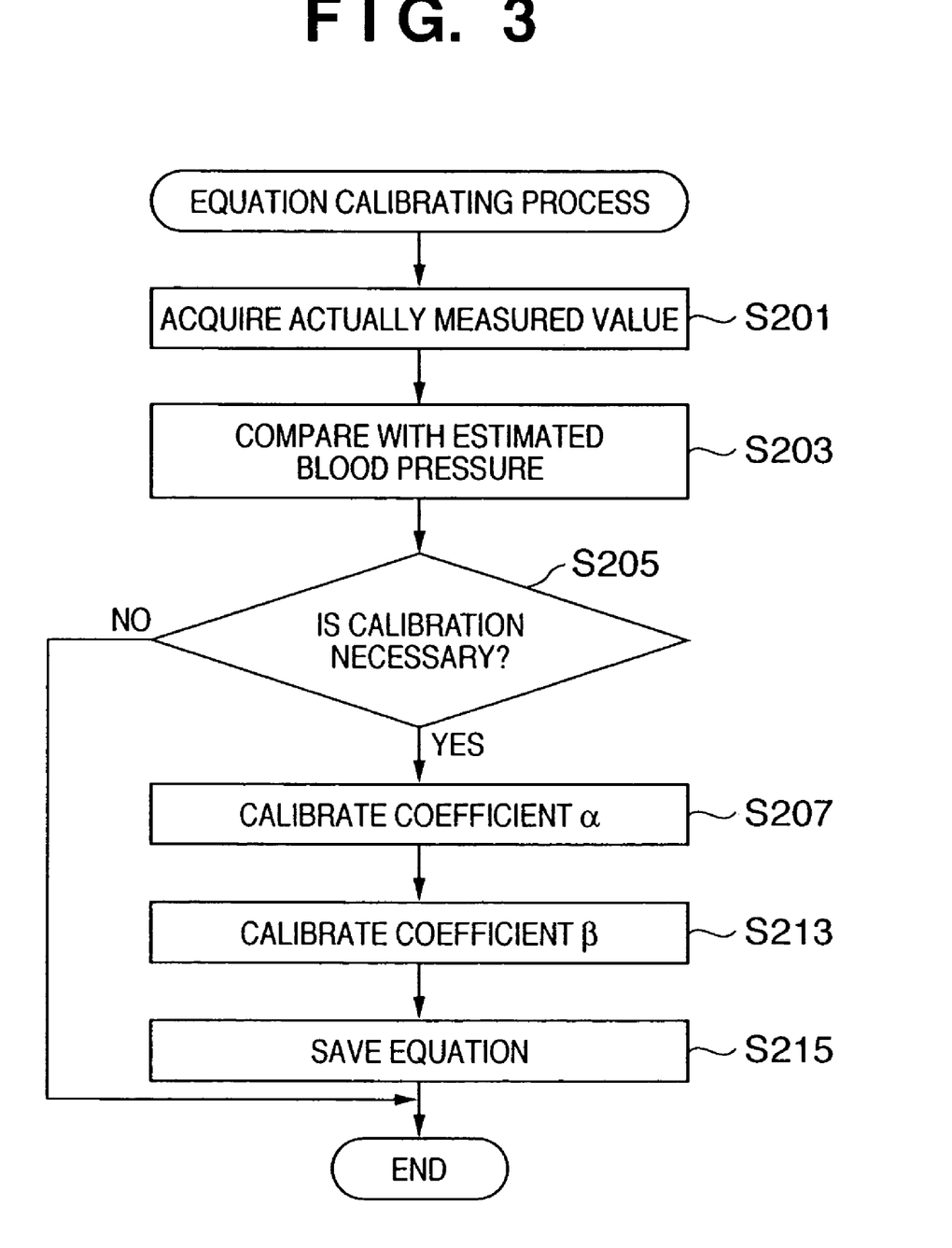
FIG. 3 is a flowchart for explaining the operation of calibrating an equation for calculating an estimated blood pressure in the biological information monitoring apparatus according to the embodiment of the present invention.

FIG. 3 is a flowchart for explaining the equation calibrating operation in the biological information monitoring apparatus of this embodiment. Similar to the blood pressure monitoring process described above, the following processing is implemented when the controller 100 executes the control program.

First, in step S201, the controller 100 acquires a blood pressure (actually measured blood pressure) measured by using a cuff. In step S203, the controller 100 compares the actually measured blood pressure with an estimated blood pressured obtained immediately before the cuff blood pressure measurement is started, or with an immediately preceding actually measured blood pressure. In step S205, the controller 100 determines, on the basis of the difference or fluctuation ratio, whether the equation for calculating the estimated blood pressure need be calibrated.

Note that if the equation for performing the correction started in step S116 is to be calibrated because the correlation between the RR interval and pulse wave propagation time (or between the RR interval and estimated blood pressure) is reversed, it is unnecessary to determine the necessity of the calibration. Accordingly, the flow immediately advances to step S207 by skipping the processes in steps S201 to S205.

As described above, it is determined in step S205 that calibration is necessary if one of the following conditions is met (if the fluctuation amount is larger than the threshold).

(Determination by Difference)

|Estimated blood pressure−actually measured blood pressure|>$Th1$

|Actually measured blood pressure $(t-1)$−actually measured blood pressure $(t)$|>$Th2$ (Determination by Fluctuation Ratio)

|(Estimated blood pressure/actually measured blood pressure)−1|>$Th3$

|(Actually measured blood pressure $(t-1)$/actually measured blood pressure $(t)$)−1|>$Th4$ If it is determined that no calibration is necessary (the accuracy of the estimated blood pressure is satisfactory), the processing is terminated.

If it is determined that calibration is necessary, the coefficient is calibrated in step S207. As described above, the coefficient a is first calibrated in accordance with the value of d which is (estimated blood pressure−actually measured blood pressure) or (actually measured blood pressure (t−1)−actually measured blood pressure (t)).

In step S213, the coefficient β is corrected by using the calibrated coefficient a (if the fluctuation in waveform parameter is not large) or the calibrated and corrected coefficient a (if the fluctuation in waveform parameter is large) and the actually measured blood pressure. The storage unit 90 stores the calibrated coefficients or the equation containing the calibrated coefficients.

After that, the calibrated equation is used to calculate the estimated blood pressure.

Figure 4:
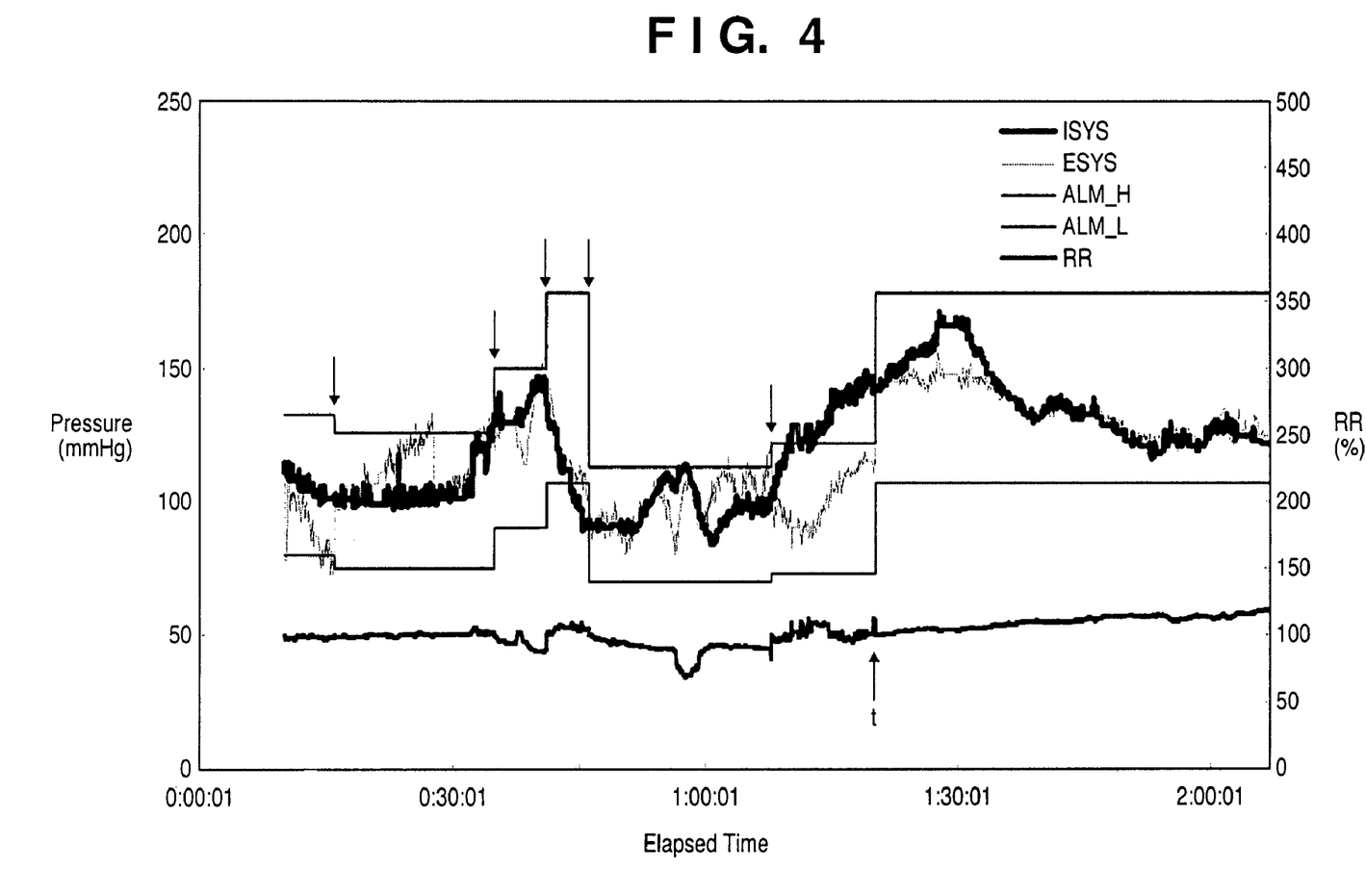
FIG. 4 is a graph showing an estimated blood pressure ESYS continuously calculated by the biological information monitoring apparatus of the embodiment, an invasively measured blood pressure ISYS, and the change rate of an RR interval.
Figure 5:
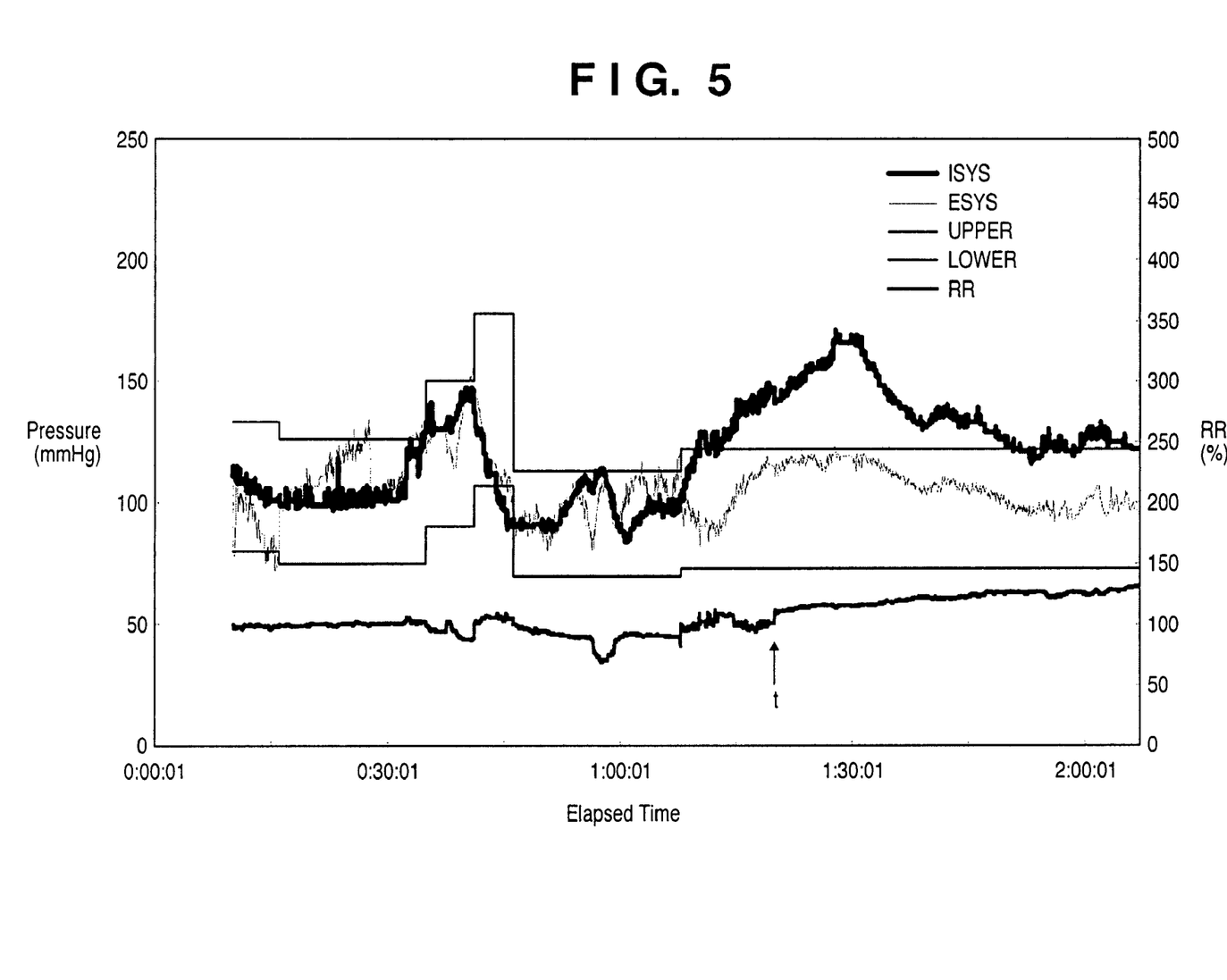
FIG. 5 is a graph showing an estimated blood pressure ESYS continuously calculated by the conventional biological information monitoring apparatus, an invasively measured blood pressure ISYS, and the change rate of an RR interval.

FIG. 4 is a graph showing an estimated blood pressure ESYS continuously calculated by the biological information monitoring apparatus of this embodiment, an invasively measured blood pressure ISYS, and the change rate of the RR interval (the increase/decrease in RR interval measured during the latest cuff blood pressure measurement). FIG. 5 is a graph showing the results of similar measurements performed by the conventional biological information monitoring apparatus. Note that the method of calibrating the coefficients a and β is applied as correction performed when the correlation between the RR interval and estimated blood pressure is reversed.

Note also that the straight lines drawn above and below the estimated blood pressure ESYS and invasively measured blood pressure ISYS indicate threshold values (e.g., the value of measured value+X% and the value of measured value−Y%) determined from the value of the latest cuff measurement.

That is, FIG. 4 shows the invasively measured blood pressure ISYS in order to show the relationship between the estimated blood pressure ESYS and the actual blood pressure, but the actual blood pressure monitoring apparatus performs no invasive measurement (if the apparatus performs invasive measurement, blood pressure estimation itself has no meaning). In practice, blood pressure measurement using a cuff is periodically performed regardless of the estimated blood pressure. In addition to this periodical measurement, cuff measurement is performed if it is determined that cuff measurement is necessary from the estimated blood pressure. During the period in which no cuff brood pressure measurement is performed, monitoring is performed using the estimated blood pressure based on the pulse wave propagation time.

FIG. 4 shows the case in which the values (e.g., the value of measured value+X% and the value of measured value−Y%) determined in accordance with the value of the latest cuff blood pressure measurement are used as the threshold values for determining whether the estimated blood pressure can be regarded as a normal value.

The values of X and Y can be arbitrary. However, when both X and Y are set smaller when the measured blood pressure is high or low than when it is not (when the measured value is normal), cuff measurement can be easily performed in response to the fluctuation in estimated blood pressure. Also, X and Y need not have the same value. For example, if the result of cuff blood pressure measurement is lower than a predetermined value, it is possible to set Y<X to make the threshold value on the decreasing side stricter (make the threshold value easier to exceed), thereby monitoring the decrease in blood pressure more strictly. On the contrary, if the cuff measurement result is high, it is possible to set X<Y to make the threshold value on the increasing side stricter.

The fluctuation amount need not be a ratio (percentage), but may also be a difference.

In the example shown in FIG. 4, it is determined that the correlation is reversed, and blood pressure measurement using a cuff is started, if a state in which both of the following two conditions are met continues for 10 pulses or more.

The estimated blood pressure ESYS has fluctuated by 50% or more the normal fluctuation determination threshold value (i.e., ESYS has fluctuated by ±10% or more from the value of the latest cuff blood pressure measurement, if the threshold value falls within the range of the value of latest cuff blood pressure measurement ±20%).

The RR interval has fluctuated in the same direction (i.e., toward the positive correlation) as the direction in which the estimated blood pressure ESYS changes, by 3% or more from the RR interval held during the latest cuff measurement.

Referring to FIG. 4, it is determined at time t that the correlation between the RR interval and estimated blood pressure ESYS is reversed, and cuff blood pressure measurement is performed. Each of the other cuff blood pressure measurements (indicated by ↓ in FIG. 4) is periodical cuff measurement or cuff measurement based on the estimated blood pressure ESYS.

In the conventional example shown in FIG. 5, the estimated blood pressure ESYS at time t falls within the range of the threshold value, so it is determined that no cuff measurement is necessary. Accordingly, the difference from the actual blood pressure (ISYS) changes without being corrected.

On the other hand, in FIG. 4 in which the necessity of cuff measurement is determined on the basis of the present invention, the difference between the invasively measured blood pressure ISYS and estimated blood pressure ESYS increases once. After that, however, the error from ISYS as an actually measured value is corrected by cuff measurement at time t.

In this embodiment as described above, the blood pressure monitoring apparatus which continuously obtains and monitors the estimated blood pressure by using the pulse wave propagation time monitors the correlation between the change in RR interval and the change in pulse wave propagation time or estimated blood pressure, and blood pressure measurement using a cuff is performed if the correlation becomes opposite to the normal state. By correcting the estimated blood pressure on the basis of the estimated error, it is possible to suppress the deterioration of the accuracy of the estimated blood pressure based on the pulse wave propagation time, thereby obtaining an accurate estimated blood pressure.

Note that in the above embodiment, the pulse wave propagation velocity is measured by using an ECG and plethysmograph in order to use an ordinary biological information monitoring apparatus. However, the present invention is also applicable to a blood pressure monitoring apparatus which calculates the pulse wave propagation velocity by another method. For example, the present invention is applicable to an apparatus which measures the pulse wave propagation time from a pulse wave measured by a cuff which is pressurized to a diastolic pressure or less and a plethysmograph, and an apparatus which measures the pulse wave propagation time from a pulse wave sensed by a pulse wave sensor and a pulse wave sensed by a cuff.

Also, in the above embodiment, the blood pressure measured by the oscillometric method using a cuff is used as the method of measuring the blood pressure for use in coefficient calibration. However, as the blood pressure to be used to calibrate the coefficients of the equation for calculating the estimated blood pressure, it is possible to use a blood pressure measured using another arbitrary blood pressure measuring method, provided that the value has accuracy to such an extent that it can be used as the reference of calibration.

Furthermore, in the above embodiment, the interval between R waves (the RR interval) is used as both the feature waveform interval in an electrocardiogram, which normally has a positive correlation with the pulse wave propagation time, and the feature waveform interval in an electrocardiogram, which normally has a negative correlation with the estimated blood pressure. However, it is also possible to use any interval between identical feature points contained in two consecutive heart beat waveforms in an electrocardiogram, e.g., it is possible to use the interval between feature waves (e.g., P waves or S waves) other than R waves, or the distance between other feature points (e.g., the leading edges of R waves). In this case, the controller 100 functions as a means for obtaining the interval between the feature points.

As many apparently widely different embodiments of the present invention can be made without departing from the spirit and scope thereof, it is to be understood that the invention is not limited to the specific embodiments thereof except as defined in the appended claims.

What is claimed is:

1. A blood pressure monitoring apparatus comprising:
    a blood pressure measuring unit adapted to measure a blood pressure by a predetermined method;
    an electrocardiogram measuring unit adapted to measure an electrocardiogram;
    a pulse wave acquiring unit adapted to acquire a pulse wave in a predetermined location of a living body;
    a pulse wave propagation time calculating unit adapted to calculate a pulse wave propagation time from the pulse wave and, one of the electrocardiogram and a pulse wave acquired from a location different from the predetermined location;
    an estimated blood pressure calculating unit adapted to calculate an estimated blood pressure by using the pulse wave propagation time;
    an interval calculating unit adapted to calculate an interval between feature points contained in two consecutive heart beat waveforms of the electrocardiogram;
    a monitoring unit adapted to monitor one of a first correlation which is a correlation between a change of the pulse wave propagation time and a change of the interval between the feature points, and a second correlation which is a correlation between a change of the estimated blood pressure and a change of the interval between the feature points; and
    a control unit adapted to perform the measurement by said blood pressure measuring unit if said monitoring unit detects that the first correlation has become a negative correlation or the second correlation has become a positive correlation, and controlling said estimated blood pressure calculating unit to correct the estimated blood pressure on the basis of a difference between the measurement result and the estimated blood pressure.

2. The apparatus according to claim 1, wherein if said monitoring unit detects one of a change of the first correlation from a negative correlation to a positive correlation, and a change of the second, correlation from a positive correlation to a negative correlation, said control unit controls said estimated blood pressure calculating unit to stop the correction of the estimated blood pressure.

3. The apparatus according to claim 1, wherein the correction adds the difference between the measurement result and the estimated blood pressure to the estimated blood pressure calculated after said blood pressure measuring unit measures the blood pressure.

4. The apparatus according to claim 1, wherein
    said estimated blood pressure calculating unit calculates the estimated blood pressure by applying the pulse wave propagation time to a predetermined equation, and
    the correction calibrates the equation on the basis of the difference between a measurement value obtained by said blood pressure measuring unit and the estimated blood pressure.

5. The apparatus according to claim 1, wherein
    said estimated blood pressure calculating unit calculates the estimated blood pressure by applying the pulse wave propagation time to a predetermined equation, and
    the blood pressure monitoring apparatus further comprises calibrating unit adapted to determine whether calibration of the equation is necessary on the basis of one of a comparison of a present measurement value and a latest measurement value obtained by said blood pressure measuring unit and a comparison of a present measurement value obtained by said blood pressure measuring unit and the estimated blood pressure, and calibrating the equation if it is determined that the calibration is necessary.

6. The apparatus according to claim 1, wherein said blood pressure measuring unit measures the blood pressure by a method incapable of continuous measurement.

7. The apparatus according to claim 1, wherein said blood pressure measuring unit measures the blood pressure by an oscillometric method using a cuff.

8. The apparatus according to claim 1, wherein said pulse wave acquiring unit acquires a plethysmograph.

9. The apparatus according to claim 1, wherein said interval calculating unit obtains an interval between R waves of the electrocardiogram as the interval between the feature points.

* * * * *